United States Patent [19]

Jones et al.

[11] Patent Number: 6,013,632
[45] Date of Patent: Jan. 11, 2000

[54] COMPOUNDS AND THEIR COMBINATIONS FOR THE TREATMENT OF INFLUENZA INFECTION

[75] Inventors: Dean P. Jones, Decatur, Ga.; Satoru Furukawa, Tokyo, Japan

[73] Assignees: Emory University, Atlanta, Ga.; Nutri-Quest, Inc., Chesterfield, Mo.

[21] Appl. No.: 09/005,747

[22] Filed: Jan. 12, 1998

Related U.S. Application Data

[60] Provisional application No. 60/035,087, Jan. 13, 1997, provisional application No. 60/035,088, Jan. 13, 1997, provisional application No. 60/034,496, Jan. 13, 1997, and provisional application No. 60/035,417, Jan. 13, 1997.

[51] Int. Cl.$^7$ ............................................. A61K 38/05
[52] U.S. Cl. ........................................ 514/17; 514/18
[58] Field of Search ........................................... 514/18, 17

[56] References Cited

U.S. PATENT DOCUMENTS

| | | |
|---|---|---|
| 3,184,505 | 5/1965 | Martin et al. . |
| 3,439,089 | 4/1969 | Cherkas . |
| 4,046,879 | 9/1977 | Swetly . |
| 4,689,347 | 8/1987 | Dinu et al. . |
| 4,867,973 | 9/1989 | Rodwell et al. . |
| 4,965,066 | 10/1990 | Hussain . |
| 5,011,678 | 4/1991 | Wang et al. . |
| 5,091,171 | 2/1992 | Yu et al. . |
| 5,135,730 | 8/1992 | Suzuki et al. . |
| 5,164,398 | 11/1992 | Sims et al. . |
| 5,208,249 | 5/1993 | Rowe et al. . |
| 5,212,079 | 5/1993 | Fujio et al. . |
| 5,238,683 | 8/1993 | Crystal . |
| 5,240,694 | 8/1993 | Gwaltney, Jr. . |
| 5,250,425 | 10/1993 | Fujio et al. . |
| 5,292,773 | 3/1994 | Hirsch et al. . |
| 5,310,567 | 5/1994 | Nakaji et al. . |
| 5,405,641 | 4/1995 | Kurihara et al. . |
| 5,422,097 | 6/1995 | Gwaltney, Jr. . |
| 5,430,045 | 7/1995 | Goldberg et al. . |
| 5,430,064 | 7/1995 | Hirsch et al. . |
| 5,455,030 | 10/1995 | Ladner et al. . |
| 5,463,029 | 10/1995 | Dunn et al. . |
| 5,464,825 | 11/1995 | Anderson et al. . |
| 5,492,689 | 2/1996 | Gwaltney, Jr. . |
| 5,516,921 | 5/1996 | Weigele et al. . |
| 5,532,215 | 7/1996 | Lezdey et al. . |
| 5,534,254 | 7/1996 | Huston et al. . |
| 5,541,297 | 7/1996 | Hansen et al. . |
| 5,554,655 | 9/1996 | Thoene . |

FOREIGN PATENT DOCUMENTS

| | | |
|---|---|---|
| 0 535 390 B1 | 4/1993 | European Pat. Off. . |
| 0 502 054 B1 | 3/1995 | European Pat. Off. . |
| 0 726 316 A2 | 8/1996 | European Pat. Off. . |
| 1268 | 4/1962 | France . |
| 3728917 | 3/1989 | Germany . |
| 4325547 | 2/1995 | Germany . |
| 01256587 | 12/1992 | Italy . |
| 8038065 | 2/1996 | Japan . |
| 1 125 675 | 8/1968 | United Kingdom . |
| WO 94/08551 | 4/1994 | WIPO . |
| WO 95/07103 | 3/1995 | WIPO . |
| WO 95/04084 | 4/1995 | WIPO . |
| WO 95/03426 | 8/1995 | WIPO . |
| WO 96/06639 | 3/1996 | WIPO . |
| WO 96/10402 | 4/1996 | WIPO . |

OTHER PUBLICATIONS

Arrick, et al., "Glutathione Metabolism as a Determinant of Therapeutic Efficacy: A Review," *Cancer Research*, 44:4224–4232 (1984).

Bitny–Szlachto, et al., "The Estimation of Oxidized and Reduced NADP by an Enzyme Reclycling System, with Oxidized Glutathione as Hydrogen Acceptor," *Acta Biochim Pol.*, 17:175–184 (1970).

Bloch, et al., "Glutathione–Isolation and Determination," *Methods in Enzymology*, 3:603–605 (Edited by Colowick and Kaplan), Published by Academic Press, Inc., New York, 1957.

Cinatl, et al., "In vitro inhibition of human cytomegalovirus replication in human foreskin fibroblasts and endothelial cells by ascorbic 2–phosphate," *Antiviral Research*, 27:405–418 (1995).

DeFlora, et al., "Attenuation of influenza–like symptomatology and improvement of cell–mediated immunity with long–term N–acetylcysteine treatment," *Eur. Respir. J.*, 10:1535–1541 (1997).

Eauclaire, "Healthy Remedies Preventing Colds and Flu," *Vegetarian Times*, (Dec. 1996).

Han, et al., "Effect of long–term dietary," Abstract 3548 (undated), No Date.

Hennet, et al., "Alterations in antioxidant defences in lung and liver of mice infected with influenza A virus," *Journal of General Virology*, 73:39–46 (1992).

Hopkins, "On Glutathione: A Reinvestigation," *The Journal of Biological Chemistry*, vol. LXXXIV, Baltimore (1929) (Edited for the American Society of Biological Chemists by Stanley R. Benedit, et al.).

Kalebic, et al., "Suppression of human immunodeficiency virus expression in chronically infected moncytic cells by glutathione, glutathione ester, and N–acetylcysteine," *Proc. Natl. Acad. Sci. USA*, 88:986–990 (1991).

Meister, et al., "Glutathione," *Ann. Rev. Biochem.*, 52:711–760 (1983).

Napier, "Nutrition Facts and Fiction About Vitamin E," *Harvard Health Letter*, vol. 22(1):1–3 (1996).

Ozawa, et al., "A New synthesis of Glutathione via the Thiazoline Peptide," *Bull. Chem. Soc. Jpn.*, 53:2592–2593 (1980).

(List continued on next page.)

*Primary Examiner*—Nathan M. Nutter
*Attorney, Agent, or Firm*—Kilpatrick Stockton LLP

[57] ABSTRACT

Administration of one or more of glutathione, its disulfide dimer, ascorbate-2-phosphate, or N-acetyl-L-cysteine, with or without antioxidants, is suitable for the treatment of influenza virus infection, as well as prophylactic prevention of influenza virus infection.

7 Claims, No Drawings

OTHER PUBLICATIONS

Palmara, et al., "Glutathione Directly Inhibits Late Stages of the Replication Cycle of HIV and Other Viruses," *Chemotherapy*, IXth International Conference on AIDS and the IVth Std. World Congress, IXth International Conference on AIDS in Affiliation with the IVth Std. World Congress, Meeting, Berlin, Germany, Jun. 6–11, 1993, 639P, IXth International Conference on AIDS, Berlin, Germany, Abstract PO–A25–0579 (1993).

Palmara, et al., "Evidence for Antiviral Acitivity of Glutathione: in Vitro Inhibition of Herpes Simplex Virus Type 1 Replication," *Antiviral Res.*, 27(3):237–253 (1995).

Robinson, "N–Acetylcysteine," *Drugs of the Future*, 20/6:559–563 (1995).

Sekine, et al., "Silyk Phosphites. 21. A New Method for the Synthesis of L–Ascorbic Acid 2–O–Phosphate[1] by Utilizing Phosphoryl Rearrangement," *J. Org. Chem.*, 47:3453–3453 (1982).

Smith, et al., "2–Methyl–2–thiazoline–4–carboxylic Acid: Formation from N–Acetylcystein and Hydrolysis," *J. Org. Chem.*, 26:820–823 (1961).

Streightoff, "In vivo Antiviral Chemotherapy: II. Anti–Influenza Action of Compounds Affecting Mucous Secretions," *Antimicrobial Agents and Chemotherapy*, 6:503–508 (1966).

Williamson and Meister, "Stimulation of hepatic glutathione formation by administration of L–2–oxothazolidine–4–carboxylate, a 5–oxo–L–prolinase substrate," *Proc. Natl. Acad. Sci. USA*, 78:936–939 (1981).

Ansel, et al., *Pharmaceutical Dosage Forms and Drug Delivery Systems*, published by Williams & Wilkins, A Waverly Company, Sixth Edition (1995).

Han, et al., "Effect of long–term dietary antioxidant supplementation on influenza infection," *The FASEB Journal*, Abstracts 1–3805 Tutorials T1–T13, Experimental Biology 97, New Orleans, Louisiana (Apr. 6–9, 1997) Abstract 3548.

The Merck Index, Eleventh Edition, p. 14 (1989).

The Merck Index, Ninth Edition, p. 579 (1976).

The Merck Index, Eleventh Editon, p. 703 (1989).

Remington's Pharmaceutical Sciences, published by Mack Publishing Company, Easton, Pennsylvania 18th Edition (1990).

"Glutathione," *Biochemical Preparations*, published by John Wiley & Sons, Inc., vol. 2:87–91 (1952).

COMPOUNDS AND THEIR COMBINATIONS FOR THE TREATMENT OF INFLUENZA INFECTION

This application claims priority to U.S. Provisional Application Ser. No. 60/035,087 filed on Jan. 13, 1997; U.S. Provisional Application Ser. No. 60/035,088 filed on Jan. 13, 1997; U.S. Provisional Application Ser. No. 60/034,496 filed on Jan. 13, 1997; and U.S. Provisional Application Ser. No. 60/035,417 filed on Jan. 13, 1997.

BACKGROUND OF THE INVENTION

Influenza virus is a large RNA virus having a core of helical symmetry containing a soluble nucleoprotein antigen. The virion has a membrane envelope with spikes containing two viral glycoproteins, one having hemagglutinating activity (HA) and one having neuraminidase activity (NA). Influenza virus attaches to a specific glycoprotein receptor for the hemagglutinin on the cell surface. The virus possesses an unusual genomic structure of RNA segments, which reshuffle upon each cycle of infection. Influenza is a virus of the respiratory tract, and is an etiological agent of acute bronchitis, pneumonia, croup, and influenza. One of the worst epidemics ever was the virus influenza epidemic early in the twentieth century. Current therapy includes amantadine, which has various undesirable side effects.

Applicants have discovered that a variety of known compounds are effective for the prevention and treatment of influenza infection. Treatment with glutathione (GSH), glutathione disulfide (GSSG), N-acetyl-L-cysteine or ascorbate-2-phosphate, or any combination thereof, with or without antioxidants, is suitable for the prevention or treatment of influenza virus infection.

Glutathione is the tripeptide gamma-L-Glu-L-Cys-Gly, of the structure

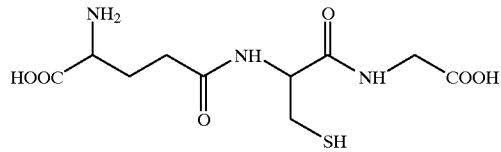

Among other natural functions, GSH is a biological reducing agent in thiol-dependent reactions. As an exogenously supplied drug, it potentiates and enhances the efficacy of various antineoplastic agents, presumably through nucleophilic thioether formation or oxidation-reduction reactions. See, e.g., Arrick, B. A. et al. *Cancer Research* 44:4224 (1984).

Glutathione (GSH) is an essential compound in the gamma-glutamyl cycle, which probably functions to transport amino acids through the cell membrane. Glutathione is also known to act as a cofactor in a variety of enzymatic reactions, including the glyoxylase reaction, the cis-trans isomerization of maleylacetoacetate to fumarylacetoacetate, and the formaldehyde dehydrogenase reaction.

Substantial evidence points to the role of GSH in reducing cellular damage from reactive oxygen species, typically generated by ionizing radiation. The exact mechanism for this effect is not understood. Intriguing evidence suggests potential therapy of certain cancers. For example, the ultimate carcinogenic form of chemical carcinogens is typically electrophiles, which can be detoxified by reactions catalyzed by GSH S-transferases. Administration of large oral dosages of GSH to rats with liver cancer results in substantial regression of the liver tumor. As noted above, GSH potentiates the efficacy of various antineoplastic agents. There is some evidence for a significant link between GSH and calcium homeostasis. For a summary of GSH metabolism, see Meister, A. et al., *Ann. Rev. Biochem.* 52:711 (1983).

Glutathione disulfide (GSSG) is the oxidized dimer of glutathione (GSH). GSSG occurs naturally in the oxidation-reduction cycle for the formation of thioethers.

N-Acetyl-L-cysteine is commonly known as a mucolytic agent. It also functions as a reducing sulfur compound in certain protein purifications, an agent for treating lower respiratory tract infections in children, as well as chronic bronchitis, HIV infection, chronic cardiorespiratory disorders and fulminant hepatic failure. It is also known as a disinfectant for Hepatitis B virus, and an agent that enhances the response to interferon-alpha in chronic Hepatitis C cases.

Ascorbate-2-phosphate is a stable derivative of ascorbic acid (vitamin C). It has the structure

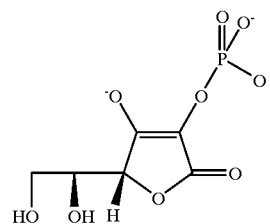

Vitamin C is widely used as an ingredient of cosmetic compositions, such as skin creams and lotions, as well as a common dietary supplement. A variety of unrelated uses are also known, including uses related to pickling and preservation of meat and seafood, improved dough for making breads, soy seasoning for fermented soybeans, sweetening agent, nerve growth factor potentiator, chemical decontaminant for a nuclear plant, a component in compositions for adding texture and color stability to frozen vegetables, an ingredient for an electroplating bath suitable for electroplating electronic parts, and part of a process for making fine palladiuum particles.

In the practice of the present invention, the antiviral agents are supplied directly to cells to reduce infection and viral particle production. Current methods for prevention of influenza infection involve immunization, which is not completely effective, is costly and has associated risks. Glutathione, glutathione disulfide, N-acetyl-L-cysteine, ascorbate-2-phosphate, or any combination thereof, are safe natural products for the treatment of influenza virus infection and also provide a novel approach to prevention. These compositions can be supplied directly to the epithelial cells which are the potential site of infection in a lozenge, drinking solution, mouth rinse or nasal spray.

BRIEF DESCRIPTION OF THE INVENTION

Applicants have discovered that certain non-toxic compounds are suitable for the prevention or treatment of infection by the influenza virus, and include compositions comprising the tripeptide analog glutathione (GSH), its oxidized dimer glutathione disulfide (GSSG), ascorbate-2-phosphate, N-acetyl-L-cysteine, or combinations thereof Delivery is preferably carried out in the form of a lozenge, drinking solution, mouth rinse or nasal spray, for the purpose of coating the nasal passages and mucous membranes of the patient.

DETAILED DESCRIPTION OF THE INVENTION

This invention relates to a pharmaceutical composition comprising
- (a) one or more compounds selected from the group consisting of glutathione, glutathione disulfide, ascorbate-2-phosphate and N-acetyl-L-cysteine, or pharmaceutically acceptable salt of any of these compounds; and
- (b) a pharmaceutically acceptable carrier, said composition useful in preventing or treating of influenza virus infection.

One embodiment of the present invention relates to the pharmaceutical composition comprising
- (a) one or more compounds selected from the group consisting of glutathione, glutathione disulfide, ascorbate-2-phosphate and N-acetyl-L-cysteine, or pharmaceutically acceptable salt of any of these compounds;
- (b) one or more antioxidants, or pharmaceutically acceptable salt of any such antioxidant; and
- (c) a pharmaceutically acceptable carrier, said composition useful in preventing or treating of influenza virus infection.

Another embodiment of the present invention relates to the pharmaceutical composition comprising
- (a) one or more compounds selected from the group consisting of glutathione, glutathione disulfide, ascorbate-2-phosphate and N-acetyl-L-cysteine, or pharmaceutically acceptable salt of any of these compounds;
- (b) one or more antioxidants selected from the group consisting of Vitamin A, Vitamin E, Vitamin K, Copper (as cupric oxide), Zinc (as zinc oxide), Iron (as ferrous salt), Selenium (sodium selenate), beta-carotene., polyphenol, catechin, quercetin, eriodictyol, carnosic acid, carnosol, rosmarrinic acid, caffeic acid, coumaric acid, cinnamic acid, Coenzyme Q10, Probucol, astaxanthin, lycopene, alpha-lipoate, and urate, or pharmaceutically acceptable salt of any such antioxidant; and
- (c) a pharmaceutically acceptable carrier, said composition useful in preventing or treating of influenza virus infection.

Another embodiment of the same invention relates to the method of treating influenza virus infection, or preventing infection by influenza virus, by administering to a patient in need of such treatment a pharmaceutical composition comprising
- (a) one or more compounds selected from the group consisting of glutathione, glutathione disulfide, ascorbate-2-phosphate and N-acetyl-L-cysteine, or pharmaceutically acceptable salt of any of these compounds; and
- (b) a pharmaceutically acceptable carrier.

Another embodiment of the same invention relates to the method of treating influenza virus infection, or preventing infection by influenza virus, by administering to a patient in need of such treatment a pharmaceutical composition comprising
- (a) one or more compounds selected from the group consisting of glutathione, glutathione disulfide, ascorbate-2-phosphate and N-acetyl-L-cysteine, or pharmaceutically acceptable salt of any of these compounds;
- (b) one or more antioxidants, or pharmaceutically acceptable salt of any such antioxidant; and
- (c) a pharmaceutically acceptable carrier.

Another embodiment of the same invention relates to the method of treating influenza virus infection, or preventing infection by influenza virus, by administering to a patient in need of such treatment a pharmaceutical composition comprising
- (a) one or more compounds selected from the group consisting of glutathione, glutathione disulfide, ascorbate-2-phosphate and N-acetyl-L-cysteine, or pharmaceutically acceptable salt of any of these compounds;
- (b) one or more antioxidants selected from the group consisting of Vitamin A, Vitamin E, Vitamin K, Copper (as cupric oxide), Zinc (as zinc oxide), Iron (as ferrous salt), Selenium (sodium selenate), beta-carotene, polyphenol, catechin, quercetin, eriodictyol, carnosic acid, carnosol, rosmarrinic acid, caffeic acid, coumaric acid, cinnamic acid, Coenzyme Q10, Probucol, astaxanthin, lycopene, alpha-lipoate, and urate, or pharmaceutically acceptable salt of any such antioxidant; and
- (c) a pharmaceutically acceptable carrier.

Another embodiment of the present invention relates to a pharmaceutical composition comprising
- (a) a compound selected from the group consisting of glutathione and glutathione disulfide, or pharmaceutically acceptable salt of any of these compounds; and
- (b) a pharmaceutically acceptable carrier, said composition useful in preventing or treating of influenza virus infection.

Another embodiment of the present invention relates to the pharmaceutical composition comprising
- (a) a compound selected from the group consisting of glutathione and glutathione disulfide, or pharmaceutically acceptable salt of any of these compounds;
- (b) one or more antioxidants; and
- (c) a pharmaceutically acceptable carrier, said composition useful in preventing or treating of influenza virus infection.

Another embodiment of the present invention relates to the pharmaceutical composition comprising
- (a) a compound selected from the group consisting of glutathione and glutathione disulfide, or pharmaceutically acceptable salt of any of these compounds;
- (b) one or more antioxidants selected from the group consisting of Vitamin A, Vitamin E, Vitamin K, Copper (as cupric oxide), Zinc (as zinc oxide), Iron (as ferrous salt), Selenium (sodium selenate), beta-carotene, polyphenol, catechin, quercetin, eriodictyol, carnosic acid, carnosol, rosmarrinic acid, caffeic acid, coumaric acid, cinnamic acid, Coenzyme Q10, Probucol, astaxanthin, lycopene, alpha-lipoate, and urate, or pharmaceutically acceptable salt of any such antioxidant; and
- (c) a pharmaceutically acceptable carrier, said composition useful in preventing or treating of influenza virus infection.

Another embodiment of the present invention relates to the method of treating influenza virus infection, or preventing infection by influenza virus, by administering to a patient in need of such treatment a pharmaceutical composition comprising
- (a) a compound selected from the group consisting of glutathione and glutathione disulfide, or pharmaceutically acceptable salt of any of these compounds; and (b) a pharmaceutically acceptable carrier.

Another embodiment of the present invention relates to the method of treating influenza virus infection, or preventing infection by influenza virus, by administering to a patient in need of such treatment a pharmaceutical composition comprising
- (a) a compound selected from the group consisting of glutathione and glutathione disulfide, or pharmaceutically acceptable salt of any of these compounds;
- (b) one or more antioxidants, or pharmaceutically acceptable salt of any such antioxidant; and
- (c) a pharmaceutically acceptable carrier.

Another embodiment of the present invention relates to the method of treating influenza virus infection, or preventing infection by influenza virus, by administering to a patient in need of such treatment a pharmaceutical composition comprising
- (a) a compound selected from the group consisting of glutathione and glutathione disulfide, or pharmaceutically acceptable salt of any of these compounds;
- (b) one or more antioxidants selected from the group consisting of Vitamin A, Vitamin E, Vitamin K, Copper (as cupric oxide), Zinc (as zinc oxide), Iron (as ferrous salt), Selenium (sodium selenate), beta-carotene, polyphenol, catechin, quercetin, eriodictyol, carnosic acid, carnosol, rosmarrinic acid, caffeic acid, coumaric acid, cinnamic acid, Coenzyme Q10, Probucol, astaxanthin, lycopene, alpha-lipoate, and urate, or pharmaceutically acceptable salt of any such antioxidant; and
- (c) a pharmaceutically acceptable carrier.

Another embodiment of this invention relates to a pharmaceutical composition comprising
- (a) ascorbate-2-phosphate or pharmaceutically acceptable salt thereof; and
- (b) a pharmaceutically acceptable carrier, said composition useful in preventing or treating of influenza virus infection.

Another embodiment of the present invention is the pharmaceutical composition comprising
- (a) ascorbate-2-phosphate or pharmaceutically acceptable salt thereof;
- (b) one or more antioxidants, or pharmaceutically acceptable salt of any such antioxidant; and
- (c) a pharmaceutically acceptable carrier, said composition useful in preventing or treating of influenza virus infection.

Another embodiment of the present invention is the pharmaceutical composition comprising
- (a) ascorbate-2-phosphate or pharmaceutically acceptable salt thereof;
- (b) one or more antioxidants selected from the group consisting of Vitamin A, Vitamin E, Vitamin K, Copper (as cupric oxide), Zinc (as zinc oxide), Iron (as ferrous salt), Selenium (sodium selenate), beta-carotene, polyphenol, catechin, quercetin, eriodictyol, carnosic acid, carnosol, rosmarrinic acid, caffeic acid, coumaric acid, cinnamic acid, Coenzyme Q10, Probucol, astaxanthin, lycopene, alpha-lipoate, and urate, or pharmaceutically acceptable salt of any such antioxidant; and
- (c) a pharmaceutically acceptable carrier, said composition useful in preventing or treating of influenza virus infection.

Another embodiment of the present invention is the method of treating influenza virus infection, or preventing infection by influenza virus, by administering to a patient in need of such treatment a pharmaceutical composition comprising
- (a) ascorbate-2-phosphate or pharmaceutically acceptable salt thereof; and
- (b) a pharmaceutically acceptable carrier.

Another embodiment of the present invention is the method of treating influenza virus infection, or preventing infection by influenza virus, by administering to a patient in need of such treatment a pharmaceutical composition comprising
- (a) ascorbate-2-phosphate or pharmaceutically acceptable salt thereof;
- (b) one or more antioxidants, or pharmaceutically acceptable salt of any such antioxidant; and
- (c) a pharmaceutically acceptable carrier.

Another embodiment of the present invention is the method of treating influenza virus infection, or preventing infection by influenza virus, by administering to a patient in need of such treatment a pharmaceutical composition comprising
- (a) ascorbate-2-phosphate or pharmaceutically acceptable salt thereof;
- (b) one or more antioxidants selected from the group consisting of Vitamin A, Vitamin E, Vitamin K, Copper (as cupric oxide), Zinc (as zinc oxide), Iron (as ferrous salt), Selenium (sodium selenate), beta-carotene, polyphenol, catechin, quercetin, eriodictyol, carnosic acid, carnosol, rosmarrinic acid, caffeic acid, coumaric acid, cinnamic acid, Coenzyme Q10, Probucol, astaxanthin, lycopene, alpha-lipoate, and urate, or pharmaceutically acceptable salt of any such antioxidant; and
- (c) a pharmaceutically acceptable carrier.

Another embodiment of this invention relates to a pharmaceutical composition comprising
- (a) N-acetyl-L-cysteine, or pharmaceutically acceptable salt thereof;
- (b) a pharmaceutically acceptable carrier, said composition useful in preventing or treating of influenza virus infection.

Another embodiment of the present invention relates to the pharmaceutical composition comprising
- (a) N-acetyl-L-cysteine, or pharmaceutically acceptable salt thereof;
- (b) one or more antioxidants, or pharmaceutically acceptable salt of any such antioxidant; and
- (c) a pharmaceutically acceptable carrier, said composition useful in preventing or treating of influenza virus infection.

Another embodiment of the present invention relates to the pharmaceutical composition comprising
- (a) N-acetyl-L-cysteine, or pharmaceutically acceptable salt thereof;
- (b) one or more antioxidants selected from the group consisting of Vitamin A, Vitamin E, Vitamin K, Copper (as cupric oxide), Zinc (as zinc oxide), Iron (as ferrous salt), Selenium (sodium selenate), beta-carotene, polyphenol, catechin, quercetin, eriodictyol, carnosic acid, carnosol, rosmarrinic acid, caffeic acid, coumaric acid, cinnamic acid, Coenzyme Q10, Probucol, astaxanthin, lycopene, alpha-lipoate, and urate, or pharmaceutically acceptable salt of any such antioxidant; and (c) a pharmaceutically acceptable carrier, said composition useful in preventing or treating of influenza virus infection.

Another embodiment of the present invention relates to the method of treating influenza virus infection, or preventing infection by influenza virus, by administering to a patient in need of such treatment a pharmaceutical composition comprising (a) N-acetyl-L-cysteine, or pharmaceutically acceptable salt thereof; and (b) a pharmaceutically acceptable carrier.

Another embodiment of the present invention relates to the method of treating influenza virus infection, or preventing infection by influenza virus, by administering to a patient in need of such treatment a pharmaceutical composition comprising (a) N-acetyl-L-cysteine, or pharmaceutically acceptable salt thereof;

(b) one or more antioxidants, or pharmaceutically acceptable salt of any such antioxidant; and (c) a pharmaceutically acceptable carrier.

Another embodiment of the present invention relates to the method of treating influenza virus infection, or preventing infection by influenza virus, by administering to a patient in need of such treatment a pharmaceutical composition comprising (a) N-acetyl-L-cysteine, or pharmaceutically acceptable salt thereof;

(b) one or more antioxidants selected from the group consisting of Vitamin A, Vitamin E, Vitamin K, Copper (as cupric oxide), Zinc (as zinc oxide), Iron (as ferrous salt), Selenium (sodium selenate), beta-carotene, polyphenol, catechin, quercetin, eriodictyol, carnosic acid, carnosol, rosmarrinic acid, caffeic acid, coumaric acid, cinnamic acid, Coenzyme Q10, Probucol, astaxanthin, lycopene, alpha-lipoate, and urate, or pharmaceutically acceptable salt of any such antioxidant; and (c) a pharmaceutically acceptable carrier.

In another embodiment of the same invention, the pharmaceutical compositions are administered as drinking solutions.

In vitro studies showed that the compositions of the present invention, when exogenously added at 10 to 30 mM, decreased infectivity and active influenza viral particle production at low multiplicity of infection in Madin-Darby canine kidney (MDCK) cells and normal human small airway epithelial cells. The compositions of the present invention protected when added after viral adherence; they did not protect when added only before or during viral adherence. They did not block synthesis of viral proteins or apoptosis in infected cells and did not protect against loss of the compositions of the present invention in infected cells. Thus, the protection against influenza infection by addition of the compositions of the present invention probably occurred by interrupting protease cleavage of the viral HA protein after particles were released. Without this inhibition, newly produced virus particles would be activated and spread the infection to other cells In vivo, influenza viral particles are released from the apical surface of the epithelial cells so that supply of these compositions at relevant concentrations to the apical surface of the nasal, oral and upper respiratory epithelia can have the same effect by inhibiting protease activation of influenza virus.

The compositions of the present invention, added directly to epithelial cells, decrease infection by influenza virus. In one respect, this invention concerns the direct use of these compositions to decrease infection and reduce production of infectious viral particles in various cell types including human airway epithelia which are a primary site of initial infection in vivo. Thus, preparation of these compositions for direct delivery to the oral, nasal and respiratory epithelia, such as lozenge, oral rinse or nasal spray, can be used to prevent influenza infection. Other thiols and antioxidants can also have this effect and those compositions in combination with other thiols or antioxidants can have an increased effect. Such preparations are expected to be useful for reduction in risk of infection in humans and in veterinary or domestic animals. Preparations for supply of these compositions directly to oral, nasal and airway epithelia may also protect against other viral infections (e.g., common cold). In principle, vaginal or rectal suppositories, salves or other preparations for direct supply of the compositions of the present invention to epithelial surfaces could reduce viral infections at other sites.

Glutathione, abbreviated GSH, and it is also commonly named as the peptide analog gamma-L-Glu-L-Cys-Gly.

The pharmaceutically-acceptable salts of the compounds (in the form of water-or oil-soluble or dispersible products) include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-napthalensulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, didbutyl; and diamyl sulfates, long chain halides such as decyl, lauryl, myristyl and stearyl chlorides, bromides and iodides, aralkyl halides like benzyl and phenethyl bromides and others. Other pharmaceutically acceptable salts include the sulfate salt ethanolate and sulfate salts.

Glutathione is synthesized by the method of Ozawa, Y. et al., *Bull. Chem. Soc. Jpn.* 53: 2592 (1980). Alternatively, glutathione is isolated from yeast by the method of Bloch, K. et al., *Methods in Enzymology* 3, 603 (1957).

Glutathione disulfide (GSSG) is synthesized by the method of Bitny-Szlachto et al., Acta Biochim. Pol. 17, 175 (1970).

Ascorbate-2-phosphate is synthesized by the methods of U.S. Pat. Nos. 5,250,425 and 5,212,079, herein incorporated by reference for these purposes. See also Sekin, M. et al., *J. Org. Chem.* 47, 3453 (1982).

N-Acetyl-L-cysteine is synthesized by the methods of Smith, *J.Org. Chem.* 26, 820 (1961), and of U.S. Pat. No. 3,184,505, herein incorporated by reference for these purposes.

For these purposes, the compositions of the present invention may be administered orally, nasally, or rectally, in dosage unit formulations containing conventional non-toxic pharmaceutically-acceptable carriers, adjuvants and vehicles.

Thus, in accordance with the present invention, there is further provided a method of treating and a pharmaceutical composition for treating influenza virus infection and prevention of influenza virus infection. The treatment involves administering to a patient in need of such treatment a pharmaceutical carrier and a therapeutically effective amount of any composition of the present invention, or a pharmaceutically acceptable salt thereof.

These pharmaceutical compositions may be in the form of orally-administrable suspensions, drinking solutions or tablets; nasal sprays or nasal drops; or olegenous suspensions or suppositories.

When administered orally as a suspension, compositions of the present invention are prepared according to techniques well-known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art. Components in the formulation of a mouthwash or rinse include antimicrobials, surfactants, cosurfactants, oils, water and other additives such as sweeteners/flavoring agents known in the art.

When administered by a drinking solution, the composition comprises one or more of the compounds of the present invention, dissolved in water, with appropriate pH adjustment, and with carrier. The compound present may range in concentration between about 10 mM and about 200 mM, preferably about 50 mM. The compound may be dissolved in distilled water, tap water, spring water, and the like. The pH is typically adjusted to between about 4.0 and 6.5, preferably about 6.0. Sweeteners may be added, e.g., 1% (w/v) sucrose.

When administered nasally, these compositions are prepared according to techniques well-known in the art of pharmaceutical formulation and may be prepared as solutions in saline, employing benzyl alcohol or other suitable preservatives, absorption promoters to enhance bioavailability, and/or other solubilizing or dispersing agents known in the art. See, for example, Ansel, H. C. et al., *Pharmaceutical Dosage Forms and Drug Delivery Systems*, Sixth Ed. (1995).

Preferably these compositions and formulations are prepared with suitable nontoxic pharmaceutically acceptable ingredients. These ingredients are known to those skilled in the preparation of nasal dosage forms and some of these can be found in REMINGTON'S PHARMACEUTICAL SCIENCES, 17th edition, 1985, a standard reference in the field. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, jelling agents, or buffering and other stabilizing and solubilizing agents may also be present. Preferably, the nasal dosage form should be isotonic with nasal secretions. For drinking solutions, sweeteners such as sucrose are preferable.

The formulations of this invention may be varied to include; (1) other acids and bases to adjust the pH; (2) other tonicity imparting agents such as sorbitol, glycerin and dextrose; (3) other antimicrobial preservatives such as other parahydroxy benzoic acid esters, sorbate, benzoate, propionate, chlorbutanol, phenylethyl alcohol, benzalkonium chloride, and mercurials; (4) other viscosity imparting agents such as sodium carboxymethylcellulose, microcrystalline cellulose, polyvinylpyrrolidone, polyvinyl alcohol and other gums; (5) suitable absorption enhancers; (6) stabilizing agents such as antioxidants, like bisulfite and ascorbate, metal chelating agents such as sodium edetate and drug solubility enhancers such as polyethylene glycols.

The above nasal formulations can be administers as drops, sprays, or by any other intranasal dosage form. Optionally, the delivery system can be a unit dose delivery system. The volume of solution or suspension delivered per dose can be anywhere from 5 to 400 microliters, and preferably 50 to 150 microliters. Delivery systems for these various dosage forms can be dropper bottles, plastic squeeze units, atomizers, and the like in either unit dose or multiple dose packages.

Lozenges can be prepared according to U.S. Pat. No. 3,439,089, herein incorporated by reference for these purposes.

When rectally administered in the form of suppositories, these compositions may be prepared by mixing the drug with a suitable non-irritating excipient, such as cocoa butter, synthetic glyceride esters or polyethylene glycols, which are solid at ordinary temperatures, but liquidity and/or dissolve in the rectal cavity to release the drug.

Dosage levels of the order of 25 mg/day to 10 g/day are useful in the treatment or prevention of the above-indicated conditions. In one preferred regimen, such dosages are administered to each patient by either nasal spray or by oral lozenge. It will be understood, however, that the specific dose level and frequency of dosage for any particular patient may be varied and will depend upon a variety of factors including the activity of the specific salt or other form employed, the metabolic stability and length of action of that compound, the age, body weight, general health, sex, diet, mode and time of administration, rate of excretion, drug combination, the severity of the particular condition, and the host undergoing therapy.

The present invention is also directed to compositions of the present invention with one or more antioxidants. For example, glutathione and glutathione disulfide, or any other composition of the present invention, may be effectively administered, whether at periods of pre-exposure or post-exposure or both, in combination with effective amounts of one or more of the antioxidants listed below:

Vitamin A,

Vitamin E,

Vitamin K,

Copper (as cupric oxide),

Zinc (zinc oxide),

Iron (Ferrous Salt),

Selenium (Sodium Selenate),

Beta-carotene, polyphenols, flavinoids, including flavanols, such as catechin or quercetin, and flavanones such as eriodictyol, Diterpenoids, such as carnosic acid, or carnosol, Phenolic acids, e.g., rosmarrinic acid, caffeic acid, coumaric acid, or cinnamic acids, Coenzyme Q10, Probucol, Carotenoids, such as astaxanthin or lycopene,
Alpha-lipoate, and
urate.

EXAMPLE 1

Organic Synthesis of Glutathione

Glutathione was synthesized by the method of Ozawa, Y. et al., *Bull. Chem. Soc. Jpn.* 53: 2592 (1980), herein incorporated by reference for these purposes. In this synthesis, N-formyl-L-2-amino-4-cyanobutyric acid ethyl ester is condensed with ethyl L-cysteinylglycinate to give (4R)-2-[(3S)-3-elthoxycarbonyl-3-(formylamino) propyl]-4-(ethoxycarbonylmethylcarbamoyl)-2-thiazoline. Subsequent saponification in aqueous acetone at about −15° C., followed by treatment with dilute $H_2SO_4$ (pH4) affords formylglutathione. Removal of the formyl group is accomplished by hydrolysis with 0.5M $H_2SO_4$, to give free GSH. Further purification, if needed, is performed by converting free GSH to its copper thiolate, which is then treated with $H_2S$ to give pure GSH.

EXAMPLE 2

Isolation of Glutathione from Yeast

GSH is precipitated out of a yeast extract with cadmium chloride by the method of Bloch, K et al., *Methods in Enzymology* 3, 603 (1957), herein incorporated by reference for these purposes. To an aliquot of yeast extract is added an equal weight of 10% TCA. The residue obtained by centrifugation is extracted twice more with half the original volume of TCA. To the combined extracts is added an amount of $CdCl_2$ solution equal to one-fourth the volume of the extracts. The solution is brought to pH 5 by addition of 10 M NaOH and then adjusted to pH 6.5 with bicarbonate. The precipitated Cd complex is kept at 0° C. for 1 hour and then washed twice with ice-cold distilled water. The precipitate is dissolved in a minimum of 2 N $H_2SO_4$ and then 3 ml of 0.5 N $H_2SO_4$ is added for each 10 mg of GSH expected. The solution is filtered if necessary and the amount of GSH present determined in an aliquot. The solution is warmed to 40° C., and $Cu_2O$ suspension containing 2.5 mg of $Cu_2O$ for each 10 mg of GSH is added dropwise with gentle shaking. The precipitate is left at 0° C. for several hours, separated by centrifugation, and washed successively two times with 0.5 N $H_2SO_4$, three times with distilled water, and two times with methanol. If the cuprous mercaptide is discolored, it may be redissolved by the addition of an excess of $Cu_2O$ suspension in 0.5 N $H_2SO_4$. After filtration, the mercaptide reprecipitates on aerating the solution. For isolation of the free tripeptide the cuprous mercaptide of GSH is decomposed in aqueous suspension by $H_2$, and the solution, after removal of copper sulfide, is brought to dryness by lyophilization.

EXAMPLE 3

Increasing Concentration of GSH Inhibited Virus Production in Madin-Darby Canine Kidney (MDCK) Cells MDCK cells are cultured in 100 mm dishes until 80% confluent. Cells were washed with phosphate-buffered saline and inoculated with Influenza A/WSN strain at a multiplicity of infection of 0.05–0.1 plaque-forming units/cell in serum-free DMEM medium for 2 hours. Cells were washed with phosphate-buffered saline and supplied with DMEM +2% FBS without or with GSH (0.1–30 mM). At 48 hours post infection, 100 µl supermatant from each dish was assayed for virus HA titer. Results showed an increasing protection against virus production over the range of 0.1 mM to 30 mM GSH. Decreased virus production was 30% at 1 mM, 60% at 5 mM and 90% at 30 mM GSH. These concentrations of GSH were not toxic to the cells.

EXAMPLE 4

GSH Protected Against Virus Infection in Normal Human Small Airway Epithelial Cells (SAEC)

SAEC were cultured until 70% confluent. Cells were washed and inoculated with influenza A/WSN strain for 2 h. After washing to remove non-adherent virus, cells were cultured for up to 72 h in medium without or with GSH and assayed for virus production by HA titer. Results showed that 30 mM GSH decreased virus production by greater than 90% in the normal human SAEC. These results were confirmed by a plaque forming assay of the number of infectious particles. Thus, the results show that GSH protects against influenza infection in human cells by decreasing the production of infections virus particles.

EXAMPLE 5

GSH Protected Against Virus Production After Initial Virus Exposure

For an individual to become infected with influenza, one or more cells must initially become infected and produce virus particles that spread the infection to other cells. Experiments were performed to determine whether incubation of virus with GSH resulted in its inactivation, whether simultaneous addition to GSH with virus inhibited virus adherence to cells, or whether addition of GSH after virus adherence inhibited virus production. Incubation of virus for 1 h with up to 30 mM GSH prior to incubation with MDCK cells had no effect on the virus production after 48 h. Thus, GSH does not directly inactivate the virus. Co-incubation of 10–30 mM GSH and virus with MDCK cells for 2 h prior to washing and subsequent incubation for 48 h resulted in no decrease in virus production. Thus, GSH does not interfere with virus adherence or incorporation into cells. However, after incubation of cells with virus, added GSH decreased HA titer at 48 h by 85%. Thus, GSH inhibits production of virus by cells so that the risk of spread of infection to other cells is decreased. In this way, GSH is suitable for preventing an individual from developing influenza.

EXAMPLE 6

GSH Inhibited Virus Production While Allowing Elimination of Virus Infected Cells GSH was found to have no effect on elimination of infected cells by apoptosis following influenza infection of MDCK cells. Almost 100% of virus infected cells showed signs of apoptosis at 48 h and this was unaffected by GSH up to 30 mM. GSH alone did not cause apoptosis. Thus, the normal process of apoptosis can eliminate infected cells and decreases the chance of spread of the virus because the GSH blocks virus production without interfering with apoptosis.

EXAMPLE 7

Increased Cellular GSH Was Not Necessary for Added GSH to Protect Against Virus Infection GSH was measured in MDCK cells after infection with influenza virus either without or with 10 mM GSH. The results showed that treatment with GSH did not increase cellular GSH in the absence of virus and did not prevent the loss of GSH in the virus-infected cells. The presence of virus had no apparent affect on loss of GSH from the medium. Thus, the effects of GSH on virus infection were probably not due to effects on intracellular GSH pools, suggesting a novel mechanism of protection.

EXAMPLE 8

Effect of GSH on Viral Protein Production

To determine whether GSH altered viral protein synthesis and processing, cells were incubated with $^{35}S$-methionine to label newly synthesized proteins following virus infection either without or with added GSH. Cells were washed and lysed in SDS-PAGE buffer. Subsequent SDS-PAGE analysis followed by autoradiography showed the characteristic labeling of viral proteins. There were no detectable differences in the patterns or amounts of proteins labeled. These results, along with results in the above examples, indicates that the mechanism of action of GSH is to prevent extracellular activation of the virus, a process which can be achieved by supply of GSH to the oral, nasal and upper airway epithelium by oral rinse, lozenge, nasal spray or aerosolizer.

EXAMPLE 9

Synthesis of Glutathione Disulfide (GSSG)

A. One equivalence of glutathione in saline is reacted with excess iodine to give about one-half equalivent of GSSG.

B. GSSG is synthesized by the methods of Bitny-Szlachto et al., Acta Biochim. Pol. 17, 175(1970). In this procedure, GSSG is prepared by aeration of GSH in buffer at pH 8 in the presence of catalytic amounts of $FeSO_4$, until negative reaction with nitroprusside occurs. Then the solution is treated with charcoal, adjusted to pH 6, concentrated under reduced pressure, and GSSG is precipitated out with ethanol.

EXAMPLE 10

Glutathione Disulfide (GSSG) Protected Against Influenza Infection by Inhibiting Virus Production MDCK cells were cultured in 100 mm dishes until 80% confluent. Cells were washed with phosphate-buffered saline and inoculated with Influenza A/WSN strain at a multiplicity of infection of 0.05–0.1 plaque-forming units/cell in serum-free DMEM medium for 2 hours. Cells were washed with phosphate-buffered saline and supplied with DMEM +2% FBS without or with GSSG. At 48 hours post infection, 100 μl supernatant from each dish was assayed for virus HA titer. Results showed that 10 mM GSSG gave 33% and 50% inhibition of virus production at 48 and 72 h, respectively. 30 mM GSSG gave 33% and 75% inhibition of virus production at 48 and 72 h, respectively. GSSG was not toxic to cells at these concentrations. Thus, GSSG protects against virus infection by inhibiting virus production.

EXAMPLE 11

Synthesis of Ascorbate-2-Phosphate

1

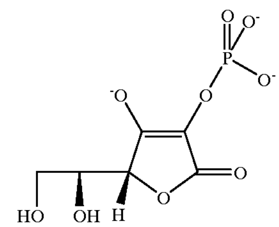

4

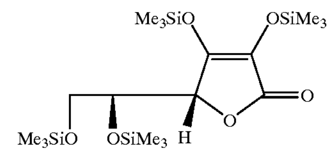

8

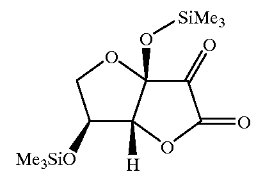

10

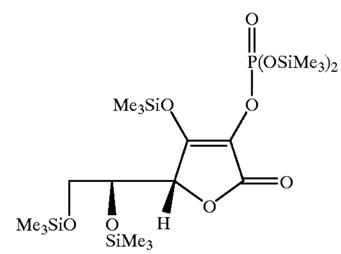

13

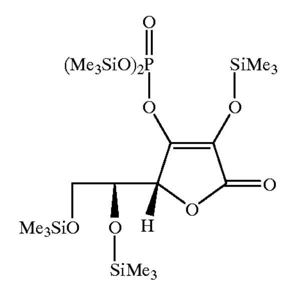

Ascorbate-2-phosphate (1), also known as ascorbate-2'-phosphate, is chemically synthesized by the method of Sekine, M. et al., *J. Org. Chem.* 47, 3453 (1982).

(A) Preparation of 2,3,5,6-Tetrakis-O-(trimethylsilyl) ascorbate (4) L-Ascorbic acid (101 g, 0.573 mol) is dissolved in 700 mL of dry pyridine. Hexamethyldisilazane (10 mL) is added to the solution, whereupon a white precipitate appears immediately. The mixture is gradually heated to 100° C., at which ammonia gas is evolved. To the mixture is further added 246 mL of hexamethyldisilazane at 100° C., so slowly that vigorous stirring can be continued. After the addition is completed, the resulting solution is heated at 100° C. for an additional 2 h. After the solution is cooled to room temperature, the solvent and the excess reagent are removed in vacuo, and distillation of the residue gives 4.

(B) Preparation of Bicyclic Lactone 8. To a solution of 4 (23.9 g, 51.4 mL, 51.4 mmol) in 50 mL of dry $CH_2CL_2$ at 0° C. is added dropwise bromine (2.63 mL, 51.4 mmol) in 8 mL of dry $CH_2CL_2$. After the mixture is stirred at room temperature for 1 h, 5.6 mL (51.4 mmol) of dimethyl phosphonate is added at 0° C., and the mixture is kept at room temperature overnight. The solution color changes from orange to red. The solvent is removed in vacuo, and the residue is distilled to afford 8.

(C) Reaction of Bicyclic Alpha-Keto Lactone 8 with TMSP. To a solution of 514 mg (1.61 mmol) of 8 in 4 mL of dry $CH_2CL_2$ at 0° C. is added 0.534 mL (1.61 mmol) of TMSP by a syringe. The solution turns immediately from yellow to colorless. After the solvent is removed in vacuo, the residue is dissolved in $CDCL_3$ and measured by $^1H$ NMR, $^{31}p$ NMR.

(D) Preparation of 10. To the bicyclic alpha-keto lactone 8 (3.48 g, 10.9 mmol) melted at 60° C. is added 3.6 mL (10.9 mmol) of TMSP. The mixture turns light yellow. The mixture is heated at 105° C. After 5 h, 8 disappears and a mixture of 10 and 13 is formed in the ratio 88:12 ($^1H$ NMR). Distillation is then performed.

(E) Tricyclohexylammonium Salt of L-Ascorbic Acid 2-0-Phosphate. The above mentioned reaction mixture (1.456 g) containing 1.0 and 13 (88:12) is dissolved in 50 mL of ether and 8 mL of methanol. After the solution is kept at room temperature for 1 h, 2 mL (17 mmol) of cyclohexylamine is added. The solution is cooled to 0° C. The precipitate is collected by filtration, washed with three 10-mL portions of ether, and dried over $P_4O_{10}$ in vacuo to give the title compound(1).

EXAMPLE 12

Ascorbate-2-phosphate Prevented Infectious Influenza Virus Production

Experiments with ascorbate-2-phosphate instead of GSH showed that 10 or 30 mM ascorbate-2-phosphate provided protection against virus titer and infectious particle production. MDCK cells were cultured in 100 mm dishes until 80% confluent. Cells were washed with phosphate-buffered saline and inoculated with Influenza A/WSN strain at a multiplicity of infection of 0.05–0.1 plaque-forming units/cell in serum-free DMEM medium for 2 hours. Cells were washed with phosphate-buffered saline and supplied with DMEM+2% FBS without or with ascorbate-2-phosphate. At 48 hours post infection, 100 µl supernatant from each dish was assayed for virus HA titer or plaque-forming units. 10 mM ascorbate-2-phosphate gave 37% inhibition of virus titer and 50% inhibition of plaque-forming units at 48 h. Ascorbate-2-phosphate was not toxic to the cells at this concentration.

EXAMPLE 13

Ascorbate-2-phosphate Plus GSH Provided Greater Protection Than Either Alone Experiments with MDCK cells and Influenza A/WSN strain at a multiplicity of infection of 0.05–0.1 plaque-forming units/cell showed that protection against influenza virus production at 48 h was greater with 10 mM each of ascorbate-2-phosphate and GSH (75% inhibition) than with either 10 mM ascorbate-2-phosphate alone (37% inhibition) or 10 mM GSH alone (56% inhibition).

EXAMPLE 14

Synthesis of N-Acetyl-L-cysteine (NAC)

N-Acetyl-L-cysteine is synthesized by the methods of Smith, *J. Org. Chem.* 26, 820 (1961). Twenty grams of cystine are dissolved in 200 ml of water containing 12 g of sodium hydroxide, and 40 ml of acetic anhydride is added dropwise with stirring and cooling in an ice bath over a period of 30 minutes. The solution is allowed to stand at room temperature 1 hr, then heated to 55° C. and zinc dust added. The solution is stirred for 15 minutes, cooled, and centrifuged to remove unchanged zinc. To a portion of the centrifugate 1 M lead acetate is added. The mercaptide is centrifuged, washed, and decomposed with hydrogen sulfide. The lead sulfide is removed by filtration and the filtrate lyophilized. Further purification is accomplished by dissolving in isopropyl alcohol followed by precipitation with dry ether, and repeating this procedure up to three times. See also U.S. Pat. No. 3,184,505, herein incorporated by reference for these purposes.

EXAMPLE 15

N-Acetyl-L-cysteine (NAC) Protected Against Influenza Infection by Inhibiting Virus Production MDCK cells were cultured in 100 mm dishes until 80% confluent. Cells were washed with phosphate-buffered saline and inoculated with Influenza A/WSN strain at a multiplicity of infection of 0.05–0.1 plaque-forming units/cell in serum-free DMEM medium for 2 hours. Cells were washed with phosphate-buffered saline and supplied with DMEM +2% FBS without or with NAC. At 48 hours post infection, 100 µl supernatant from each dish was assayed for virus HA titer. Results showed that 10 mM NAC gave 50% and 62% inhibition of virus production at 24 and 48 h., respectively. 30 mM NAC gave 75% and 95% inhibition of virus production at 24 and 48 h., respectively. NAC was not toxic to cells at these concentrations. Thus, NAC protects against virus infection by inhibiting virus production.

EXAMPLE 16

Preparation of Nasal Spray for Glutathione or GSSG Treatment

A nasal spray containing glutathione or GSSG was prepared by adding 3 mg of glutathione or GSSG per milliliter of saline (0.9% NaCl, w/v in water).

EXAMPLE 17

Preparation of Nasal Solution Composition for GSH Treatment

| A nasal spray is prepared, containing | |
|---|---|
| Glutathione | 1.0 g |
| Sodium Acetate | 0.3 g |
| Methylparaben | 0.1 g |
| Propylparaben | 0.02 g |
| Sodium Chloride | As needed for tonicity |
| HCl or NaOH | To adjust pH |
| Purified Water | to 100 ml. |

EXAMPLE 18

Preparation of Nasal Solution Composition for GSSG Treatment

| A nasal spray is prepared, containing | |
|---|---|
| GSSG | 1.0 g |
| Sodium Acetate | 0.3 g |
| Methylparaben | 0.1 g |
| Propylparaben | 0.02 g |
| Sodium Chloride | As needed for tonicity |
| HCl or NaOH | To adjust pH |
| Purified Water | to 100 ml. |

EXAMPLE 19

Preparation of Cough Drops Containing Glutathione

| Candy Base: | | |
|---|---|---|
| Sugar (medium fine granules) | kg | 35.0 |
| Corn syrup 43° Baumé | kg | 21.0 |
| Medicament Mixture: | | |
| Polyethylene glycol (6,000 m.w.) | kg | 2.75 |
| Glutathione | kg | 5.0 |
| Citric Acid | kg | 60 |
| Wild cherry imitation flavor | gm | 60.0 |

In preparing the candy base, the sugar is dissolved in 5.5 liters of water, and the glucose-containing corn syrup is added and mixed well. At this point, any desired dye may be added to impart the required color. The dye must be dissolved thoroughly.

The above mixture is placed in a steamjacketed kettle which is heated to 125° C. from which it is pumped into a storage vessel that feeds a continuous cooker. As the syrup passes through a coil in the cooker, it reaches a temperature of 125–150° C. and is then fed into a receiving kettle maintained at 28–29 inches of vacuum by means of a steam vacuum ejector for a period of about 6–7 minutes. During this period water is removed until it is reduced to about 1% or less and a suitable molten candy base is formed. The candy base then is permitted to cool slowly.

The medicament, citric acid and imitation flavor in powdered form are added to the polyethylene glycol and the mixture then fluidized by heating at about 90° C. The hot fluid mixture is rapidly added to the molten candy base (the temperature of which has been reduced to about 100° C. or slightly below) with adequate mixing. The total mass then is kneaded thoroughly and subsequently transferred to a spinning machine which extrudes it into lozenge forming dies. Alternatively, the medicated molten candy mass is poured onto cooling tables where it solidifies to a semi-solid mass which then may be formed into any desired shape for dispensing a unit dosage of the medicament.

EXAMPLE 20

Preparation of Cough Drops Containing GSSG

| Candy Base: | | |
|---|---|---|
| Sugar (medium fine granules) | kg | 35.0 |
| Corn syrup 43° Baumé | kg | 21.0 |
| Medicament Mixture: | | |
| Polyethylene glycol (6,000 m.w.) | kg | 2.75 |
| GSSG | kg | 5.0 |
| Citric Acid | kg | 60 |
| Wild cherry imitation flavor | gm | 60.0 |

In preparing the candy base, the sugar is dissolved in 5.5 liters of water, and the glucose-containing corn syrup is added and mixed well. At this point, any desired dye may be added to impart the required color. The dye must be dissolved thoroughly.

The above mixture is placed in a steamjacketed kettle which is heated to 125° C. from which it is pumped into a storage vessel that feeds a continuous cooker. As the syrup passes through a coil in the cooker, it reaches a temperature of 125–150° C. and is then fed into a receiving kettle maintained at 28–29 inches of vacuum by means of a steam vacuum ejector for a period of about 6–7 minutes. During this period water is removed until it is reduced to about 1% or less and a suitable molten candy base is formed. The candy base then is permitted to cool slowly.

The medicament, citric acid and imitation flavor in powdered form are added to the polyethylene glycol and the mixture then fluidized by heating at about 90° C. The hot fluid mixture is rapidly added to the molten candy base (the temperature of which has been reduced to about 100° C. or slightly below) with adequate mixing. The total mass then is kneaded thoroughly and subsequently transferred to a spinning machine which extrudes it into lozenge forming dies. Alternatively, the medicated molten candy mass is poured onto cooling tables where it solidifies to a semi-solid mass which then may be formed into any desired shape for dispensing a unit dosage of the medicament.

EXAMPLE 21

Preparation of Nasal Spray for Ascorbate-2-Phosphate Treatment

A nasal spray containing ascorbate-2-phosphate was prepared by adding 3 mg of glutathione per milliliter of saline (0.9% NaCl, w/v in water).

EXAMPLE 22

Preparation of Nasal Solution Composition for Ascorbate-2-Phosphate Treatment

| A nasal spray is prepared, containing | |
|---|---|
| Ascorbate-2-Phosphate | 1.0 g |
| Sodium Acetate | 0.3 g |
| Methylparaben | 0.1 g |
| Propylparaben | 0.02 g |
| Sodium Chloride | As needed for tonicity |
| HCl or NaOH | To adjust pH |
| Purified Water | to 100 ml. |

EXAMPLE 23

Preparation of Cough Drops Containing Ascorbate-2-Phosphate

| Candy Base: | | |
|---|---|---|
| Sugar (medium fine granules) | kg | 35.0 |
| Corn syrup 43° Baumé | kg | 21.0 |
| Medicament Mixture: | | |
| Polyethylene glycol (6,000 m.w.) | kg | 2.75 |
| Ascorbate-2-Phosphate | kg | 5.0 |
| Citric Acid | kg | 60 |
| Wild cherry imitation flavor | gm | 60.0 |

In preparing the candy base, the sugar is dissolved in 5.5 liters of water, and the glucose-containing corn syrup is added and mixed well. At this point, any desired dye may be added to impart the required color. The dye must be dissolved thoroughly.

The above mixture is placed in a steamjacketed kettle which is heated to 125° C. from which it is pumped into a storage vessel that feeds a continuous cooker. As the syrup passes through a coil in the cooker, it reaches a temperature of 125–150° C. and is then fed into a receiving kettle maintained at 28–29 inches of vacuum by means of a steam vacuum ejector for a period of about 6–7 minutes. During this period water is removed until it is reduced to about 1% or less and a suitable molten candy base is formed. The candy base then is permitted to cool slowly.

The medicament, citric acid and imitation flavor in powdered form are added to the polyethylene glycol and the mixture then fluidized by heating at about 90° C. The hot fluid mixture is rapidly added to the molten candy base (the temperature of which has been reduced to about 100° C. or slightly below) with adequate mixing. The total mass then is kneaded thoroughly and subsequently transferred to a spinning machine which extrudes it into lozenge forming dies. Alternatively, the medicated molten candy mass is poured onto cooling tables where it solidifies to a semi-solid mass which then may be formed into any desired shape for dispensing a unit dosage of the medicament.

EXAMPLE 24

Preparation of Nasal Spray for N-Acetyl-L-Cysteine Treatment

A nasal spray containing N-acetyl-L-Cysteine was prepared by adding 3 mg of N-acetyl-L-Cysteine per milliliter of saline (0.9% NaCl, w/v in water).

EXAMPLE 25

Preparation of Nasal Solution Composition for N-Acetyl-L-Cysteine Treatment

| A nasal spray is prepared, containing | |
|---|---|
| N-Acetyl-L-Cysteine | 1.0 g |
| Sodium Acetate | 0.3 g |
| Methylparaben | 0.1 g |
| Propylparaben | 0.02 g |
| Sodium Chloride | As needed for tonicity |
| HCl or NaOH | To adjust pH |
| Purified Water | to 100 ml. |

EXAMPLE 26

Preparation of Cough Drops Containing N-Acetyl-L-Cysteine

| Candy Base: | | |
|---|---|---|
| Sugar (medium fine granules) | kg | 35.0 |
| Corn syrup 43° Baumé | kg | 21.0 |
| Medicament Mixture: | | |
| Polyethylene glycol (6,000 m.w.) | kg | 2.75 |
| N-Acetyl-L-Cysteine | kg | 5.0 |
| Citric Acid | kg | 60 |
| Wild cherry imitation flavor | gm | 60.0 |

In preparing the candy base, the sugar is dissolved in 5.5 liters of water, and the glucose-containing corn syrup is added and mixed well. At this point, any desired dye may be added to impart the required color. The dye must be dissolved thoroughly.

The above mixture is placed in a steamjacketed kettle which is heated to 125° C. from which it is pumped into a storage vessel that feeds a continuous cooker. As the syrup passes through a coil in the cooker, it reaches a temperature of 125–150° C. and is then fed into a receiving kettle maintained at 28–29 inches of vacuum by means of a steam vacuum ejector for a period of about 6–7 minutes. During this period water is removed until it is reduced to about 1% or less and a suitable molten candy base is formed. The candy base then is permitted to cool slowly.

The medicament, citric acid and imitation flavor in powdered form are added to the polyethylene glycol and the mixture then fluidized by heating at about 90° C. The hot fluid mixture is rapidly added to the molten candy base (the temperature of which has been reduced to about 100° C. or slightly below) with adequate mixing. The total mass then is kneaded thoroughly and subsequently transferred to a spinning machine which extrudes it into lozenge forming dies. Alternatively, the medicated molten candy mass is poured onto cooling tables where it solidifies to a semi-solid mass which then may be formed into any desired shape for dispensing a unit dosage of the medicament.

EXAMPLE 27

Preparation of Nasal Spray for Combination Treatment

A nasal spray containing glutathione and N-acetyl-L-Cysteine was prepared by adding 1.0 mg of glutathione and 2.0 mg N-acetyl-L-Cysteine, each per milliliter of saline (0.9% NaCl, w/v in water).

EXAMPLE 28

Preparation of Nasal Solution Composition for Treatment with Combination of GSSG and Ascorbate-2-Phosphate

| A nasal spray is prepared, containing | |
|---|---|
| Ascorbate-2-phosphate | 0.5 g |
| GSSG | 0.5 g |
| Sodium Acetate | 0.3 g |
| Methylparaben | 0.1 g |
| Propylparaben | 0.020 g |

-continued

| A nasal spray is prepared, containing | |
|---|---|
| Sodium Chloride | as needed for tonicity |
| HCl or NaOH | to adjust pH |
| Purified Water | to 100 ml. |

EXAMPLE 29

Preparation of Nasal Solution Composition for Treatment with Combination of GSH and GSSG

| A nasal spray is prepared containing | |
|---|---|
| GSSG | 0.5 g |
| GSH | 0.5 g |
| Sodium Acetate | 0.3 g |
| Methylparaben | 0.1 g |
| Propylparaben | 0.020 g |
| Sodium Chloride | As needed for tonicity |
| HCl or NaOH | To adjust pH |
| Purified Water | To 100 ml. |

EXAMPLE 30

Preparation of Cough Drops Containing Ascorbate-2-Phosphate and N-Acetyl-L-Cysteine

| Candy base: | | |
|---|---|---|
| Sugar (medium fine granules) | kg | 35.0 |
| Corn syrup 43° Baume | kg | 21.0 |
| Medicament mixture: | | |
| Polyethylene glycol (6,000 m.w.) | kg | 2.75 |
| Ascorbate-2-phosphate | kg | 2.5 |
| N-Acetyl-L-Cysteine | kg | 2.5 |
| Citric acid | kg | 6.0 |
| Wild cherry imitation flavor | gm | 60.0 |

In preparing the candy base, the sugar is dissolved in 5.5 liters of water, and the glucose-containing corn syrup is added and mixed well. At this point, any desired dye may be added to impart the required color. The dye must be dissolved thoroughly.

The above mixture is placed in a steamjacketed kettle which is heated to 125° C., from which it is pumped into a storage vessel that feeds a continuous cooker. As the syrup passes through a coil in the cooker, it reaches a temperature of 125–150° C., and is then fed into a receiving kettle maintained at 28–29 inches of vacuum by means of a steam vacuum ejector for a period of about 6–7 minutes. During this period water is removed until it is reduced to about 1% or less and a suitable molten candy base is formed. The candy base then is permitted to cool slowly.

The medicament, citric acid and imitation flavor in powered form are added to the polyethylene glycol and the mixture then fluidized by heating at about 90° C. The hot fluid mixture is rapidly added to the molten candy base (the temperature of which has been reduced to about 100° C., or slightly below) with adequate mixing. The total mass then is kneaded thoroughly and subsequently transferred to a spinning machine which extrudes it into lozenge forming dies. Alternatively, the medicated molten candy mass is poured onto cooling tables where it solidifies to a semi-solid mass, which then may be formed into any desired shape for dispensing a unit dosage of the medicament.

EXAMPLE 31

Preparation of Cough Drops Containing GSH and Ascorbate-2-Phosphate

| Candy base; | | |
|---|---|---|
| Sugar (medium fine granules) | kg | 35.0 |
| Corn syrup 43° Baume | kg | 21.0 |
| Medicament mixture: | | |
| Polyethylene glycol (6,000 m.w.) | kg | 2.75 |
| GSH | kg | 2.5 |
| Ascorbate-2-phosphate | kg | 2.5 |
| Citric acid | kg | 6.0 |
| Wild cherry imitation flavor | gm | 60.0 |

In preparing the candy base, the sugar is dissolved in 5.5 liters of water, and the glucose-containing corn syrup is added and mixed well. At this point, any desired dye may be added to impart the required color. The dye must be dissolved thoroughly.

The above mixture is placed in a steamjacketed kettle which is heated to 125° C., from which it is pumped into a storage vessel that feeds a continuous cooker. As the syrup passes through a coil in the cooker, it reaches a temperature of 125–150° C., and is then fed into a receiving kettle maintained at 28–29 inches of vacuum by means of a steam vacuum ejector for a period of about 6–7 minutes. During this period water is removed until it is reduced to about 1% or less and a suitable molten candy base is formed. The candy base then is permitted to cool slowly.

The medicament, citric acid and imitation flavor in powered form are added to the polyethylene glycol and the mixture then fluidized by heating at about 90° C. The hot fluid mixture is rapidly added to the molten candy base (the temperature of which has been reduced to about 100° C., or slightly below) with adequate mixing. The total mass then is kneaded thoroughly and subsequently transferred to a spinning machine which extrudes it into lozenge forming dies. Alternatively, the medicated molten candy mass is poured onto cooling tables where it solidifies to a semi-solid mass, which then may be formed into any desired shape for dispensing a unit dosage of the medicament.

While the foregoing specification teaches the principles of the present invention, with examples provided for the purpose of illustration, it will be understood that the practice of the invention encompasses all of the usual variations, adaptations, modifications or deletions as come within the scope of the following claims and its equivalents.

What is claimed is:

1. A pharmaceutical composition suitable for oral, nasal or rectal administration comprising
   (a) glutathione, or a pharmaceutically acceptable salt thereof; and
   (b) a pharmaceutically acceptable carrier suitable for oral, nasal or rectal administration,
said composition useful in preventing or treating influenza virus infection.

2. The pharmaceutical composition of claim 1, further comprising one or more antioxidants.

3. The pharmaceutical composition of claim 2, wherein the antioxidant is selected from the group consisting of Vitamin A, Vitamin E, Vitamin K, cupric oxide, zinc oxide, ferrous salts, sodium selenate, beta-carotene, polyphenol, catechin, quercetin, eriodictyol, carnosic acid, carnosol, rosmarrinic acid, caffeic acid, coumaric acid, cinnamic acid, Coenzyme Q10, Probucol, astaxanthin, lycopene, alpha-lipoate, and urate, or a pharmaceutically acceptable salt of any such antioxidant.

4. The pharmaceutical composition according to claim 1, which is in a form selected from the group consisting of a lozenge, a cough drop, a tablet, an oral rinse, a drinking solution, nasal drops, a nasal spray, an oleaginous suspension, and a suppository.

5. A pharmaceutical composition suitable for oral, nasal or rectal administration comprising
   (a) glutathione disulfide, or a pharmaceutically acceptable salt thereof; and
   (b) a pharmaceutically acceptable carrier,
said composition useful in preventing or treating influenza virus infection.

6. The pharmaceutical composition of claim 5, further comprising one or more antioxidants, or a pharmaceutically acceptable salt of any such antioxidant.

7. The pharmaceutical composition of claim 6, wherein the antioxidant is selected from the group consisting of Vitamin A, Vitamin E, Vitamin K, cupric oxide, zinc oxide, ferrous salts, sodium selenate, beta-carotene, polyphenol, catechin, quercetin, eriodictyol, carnosic acid, carnosol, rosmarrinic acid, caffeic acid, coumaric acid, cinnamic acid, Coenzyme Q10, Probucol, astaxanthin, lycopene, alpha-lipoate, and urate, or a pharmaceutically acceptable salt of any such antioxidant.

* * * * *